US010914936B2

(12) United States Patent
Tsuyuki

(10) Patent No.: US 10,914,936 B2
(45) Date of Patent: Feb. 9, 2021

(54) ENDOSCOPE AND IMAGE PICKUP APPARATUS

(71) Applicant: OLYMPUS CORPORATION, Hachioji (JP)

(72) Inventor: Hiroshi Tsuyuki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/579,601

(22) Filed: Sep. 23, 2019

(65) Prior Publication Data

US 2020/0018947 A1    Jan. 16, 2020

Related U.S. Application Data

(63) Continuation of application No. PCT/JP2017/047132, filed on Dec. 27, 2017.

(30) Foreign Application Priority Data

Mar. 24, 2017    (JP) ................. 2017-059443

(51) Int. Cl.
*G02B 23/24*    (2006.01)
*H04N 5/225*    (2006.01)
*G02B 21/18*    (2006.01)

(52) U.S. Cl.
CPC ......... *G02B 23/2446* (2013.01); *G02B 21/18* (2013.01); *H04N 5/2254* (2013.01); *H04N 2005/2255* (2013.01)

(58) Field of Classification Search
CPC .............. G02B 23/2446; G02B 21/18; H04N 2005/2255; H04N 5/2254
See application file for complete search history.

(56) References Cited

U.S. PATENT DOCUMENTS

| 8,922,634 B2 | 12/2014 | Namii |
| 9,030,543 B2 | 5/2015 | Tsuyuki et al. |

(Continued)

FOREIGN PATENT DOCUMENTS

| JP | S52104934 U | 9/1977 |
| JP | S60243604 A | 12/1985 |

(Continued)

OTHER PUBLICATIONS

International Preliminary Report on Patentability (IPRP) dated Oct. 3, 2019, issued in International Application No. PCT/JP2017/047132.

(Continued)

*Primary Examiner* — Shawn S An
(74) *Attorney, Agent, or Firm* — Holtz, Holtz & Volek PC

(57) ABSTRACT

An endoscope includes in order from an object side to an image side, an objective optical system, an optical-path splitter which splits light from the objective optical system into two, and an image sensor which picks up two split images.

A multi-order λ/4 wavelength plate made of a birefringent material is disposed in an optical path between the objective optical system and the optical-path splitter, and
the multi-order λ/4 wavelength plate satisfies the following conditional expressions (1) and (2)'.

$$10 \leq (d/d0) \times 0.25 \leq 85 \quad (1)$$

$$0.08 < |\Delta n| < 0.24 \quad (2)'$$

where,
d denotes a thickness of the multi-order λ/4 wavelength plate,
d0 denotes a thickness of the multi-order λ/4 wavelength plate, which becomes zero-order for an e-line, and (Continued)

Δn denotes a birefringence for the e-line of the multi-order λ/4 wavelength plate.

8 Claims, 8 Drawing Sheets

(56) References Cited

U.S. PATENT DOCUMENTS

| | | | |
|---|---|---|---|
| 10,054,816 B2 | 8/2018 | Koike et al. | |
| 10,205,888 B2 | 2/2019 | Tsuyuki et al. | |
| 2004/0145734 A1* | 7/2004 | Shibata | G01N 21/956 356/237.5 |
| 2011/0013186 A1* | 1/2011 | Miki | G02B 21/0064 356/364 |
| 2012/0229732 A1 | 9/2012 | Koike et al. | |
| 2013/0235174 A1 | 9/2013 | Namii | |
| 2014/0176692 A1 | 6/2014 | Tsuyuki et al. | |
| 2015/0002646 A1 | 1/2015 | Namii | |
| 2017/0187943 A1* | 6/2017 | Tsuyuki | A61B 1/00188 |
| 2019/0004367 A1 | 1/2019 | Koike et al. | |
| 2020/0015656 A1* | 1/2020 | Tsuyuki | A61B 1/00009 |

FOREIGN PATENT DOCUMENTS

| | | |
|---|---|---|
| JP | H02211404 A | 8/1990 |
| JP | 2014524290 A | 9/2014 |
| WO | 2011058774 A1 | 5/2011 |
| WO | 2013027459 A1 | 2/2013 |
| WO | 2014002740 A1 | 1/2014 |
| WO | 2016043107 A1 | 3/2016 |

OTHER PUBLICATIONS

"Depolarization Simulation", OJI Scientific Instruments, Jan. 2014, <http://www.oji-keisoku.co.jp/products/kobra/img/gijutu54.pdf>, pp. 1-7.

International Search Report (ISR) dated Mar. 27, 2018 (and English translation thereof) issued in International Application No. PCT/JP2017/047132.

Japanese Office Action dated Dec. 12, 2018 (and English translation thereof) issued in counterpart Japanese Patent Application No. JP 2018-552269.

Written Opinion of the International Searching Authority dated Mar. 27, 2018 issued in International Application No. PCT/JP2017/047132.

* cited by examiner

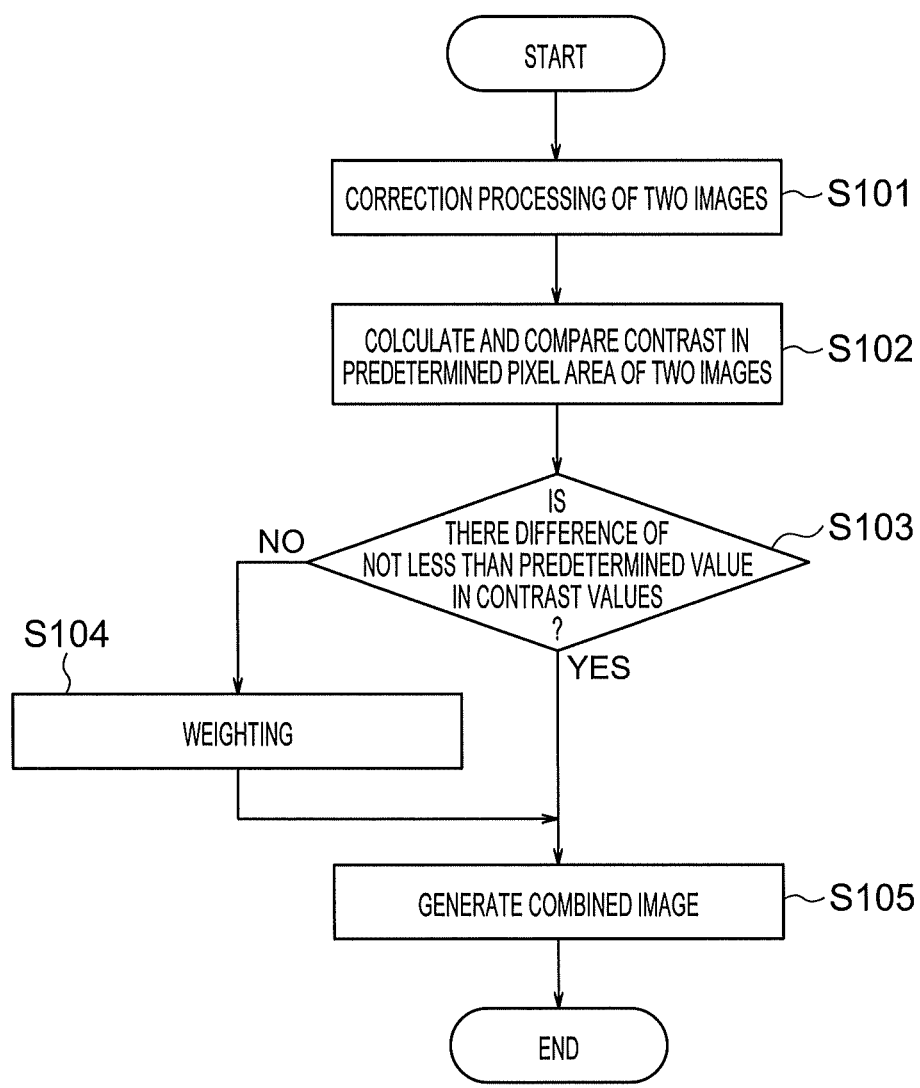

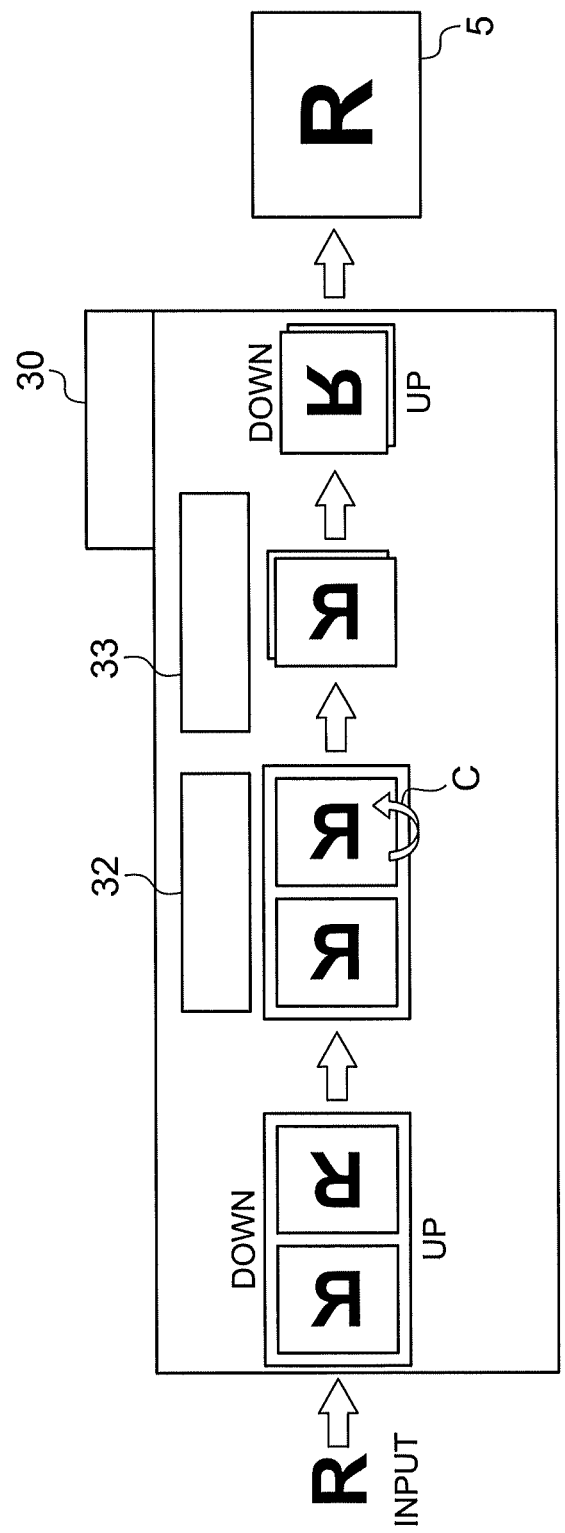

ENDOSCOPE AND IMAGE PICKUP APPARATUS

CROSS-REFERENCE TO RELATED APPLICATION

The present application is a continuation application of PCT/JP2017/047132 filed on Dec. 27, 2017 which is based upon and claims the benefit of priority from Japanese Patent Application No. 2017-059443 filed on Mar. 24, 2017; the entire contents of which are incorporated herein by reference.

BACKGROUND

Technical Field

The disclosure relates to an endoscope and an image pickup apparatus.

Description of the Related Art

Generally, in an instrument including an image sensor, such as an endoscope system, it has been known that a depth of field narrows with an increase in the number of pixels of the image sensor. In other words, in an image sensor, since a diameter of a permissible circle of confusion also becomes small with a pixel pitch (horizontal and vertical dimension of one pixel) becoming small, a depth of field of an image pickup apparatus becomes narrow.

For widening the depth of field, an arrangement in which an image is divided and images are formed, and images acquired are combined by image processing and the depth is widened, has been proposed. Here, at the time of splitting the image, using an optical-path splitter in which polarization is used is effective. In the optical-path splitter in which polarization is used, it is desirable to make depolarized light incident on the optical-path splitter. An arrangement of an element and an arrangement of an apparatus which change such polarization state to a depolarization state have been disclosed in Japanese Patent Application Laid-open Publication No. Sho-60-243604, Japanese Patent Application Laid-open Publication No. Hei 02-211404, Japanese Patent Application Laid-open Publication No. Sho-52-104934, Japanese Patent Application Laid-open Publication No. 2014-524290, International Unexamined Patent Application Publication No. 2013/027459, International Unexamined Patent Application Publication No. 2016/043107, International Unexamined Patent Application Publication No. 2014/002740.

SUMMARY

An endoscope and an image pickup apparatus according to at least some embodiments includes in order from an object side to an image side, an objective optical system, an optical-path splitter which splits light from the objective optical system into two, and an image sensor which picks up two split images, wherein a $\lambda/4$ wavelength plate made of a birefringent material is disposed in an optical path between the objective optical system and the optical-path splitter, and the $\lambda/4$ wavelength plate satisfies the following conditional expressions (1) and (2)'.

$$10 \leq (d/d0) \times 0.25 \leq 85 \quad (1)$$

$$0.08 < |\Delta n| < 0.24 \quad (2)'$$

where, d denotes a thickness of the $\lambda/4$ wavelength plate, d0 denotes a thickness of the $\lambda/4$ wavelength plate, which becomes zero-order for an e-line, and $\Delta n$ denotes a birefringence for the e-line of the $\lambda/4$ wavelength plate.

BRIEF DESCRIPTION OF THE DRAWINGS

FIG. 7 is a flowchart showing a flow in a case of combining two optical images, in the endoscope system according to the embodiment.

FIG. 8 is a diagram showing a state of image formation in a case in which an image is formed on an image sensor upon reflection for the odd number of times by a beam splitter, in the endoscope system according to the embodiment. FIG. 9A is a cross-sectional view in a normal observation state and FIG. 9B is a cross-sectional view in a close observation state.

DETAILED DESCRIPTION

An endoscope (image pickup apparatus) according to an embodiment will be described below in detail by referring to the accompanying diagrams. However, the present invention is not restricted to the embodiment described below.

Figure 1:
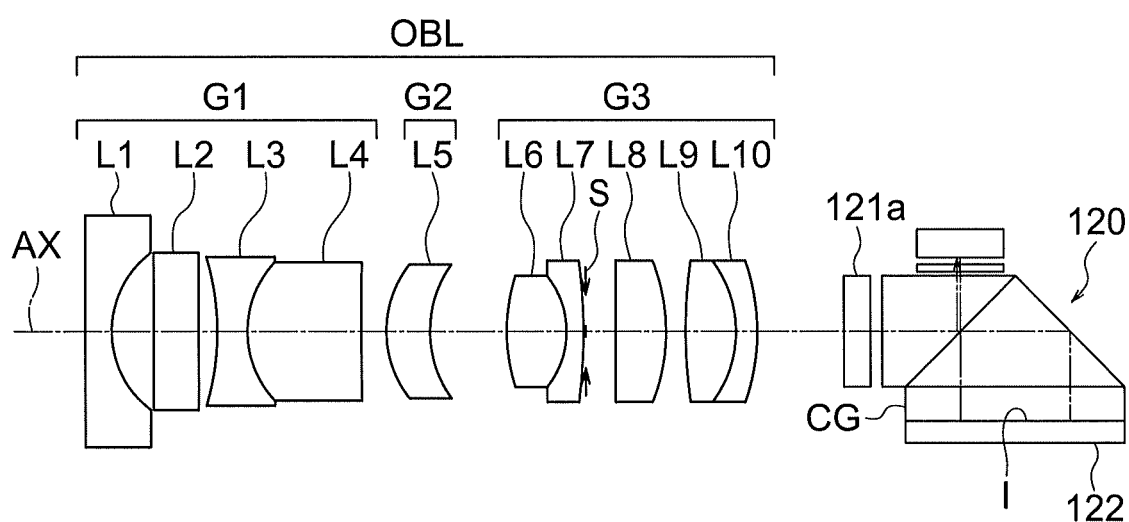
FIG. 1 is a cross-sectional view showing an arrangement of an objective optical system, an optical-path splitter, and an image sensor in an endoscope (an image pickup apparatus) (normal observation state) according to an embodiment.

FIG. 1 shows a schematic arrangement of the endoscope (image pickup apparatus) according to the present embodiment. The endoscope includes in order from an object side to an image side, an objective optical system OBL, an optical-path splitter 120 which splits light from the objective optical system OBL into two, and an image sensor 122 which picks up two split images, and a multi-order $\lambda/4$ wavelength plate 121a made of a birefringent material is disposed in an optical path between the objective optical system OBL and the optical-path splitter 120, and the multi-order $\lambda/4$ wavelength plate 121a satisfies the following conditional expressions (1) and (2).

$$10 \leq (d/d0) \times 0.25 \leq 85 \quad (1)$$

$$0.09 < |\Delta n| < 0.23 \quad (2)$$

where, d denotes a thickness of λ/4 wavelength plate, d0 denotes a thickness of the λ/4 wavelength plate, which becomes zero-order for an e-line, and Δn denotes a birefringence for the e-line of the λ/4 wavelength plate.

In the present embodiment, the multi-order λ/4 wavelength plate 121a made of a birefringent material is disposed between the objective optical system OBL and the optical-path splitter 120. Accordingly, it is possible to make light incident on the optical-path splitter 120 unpolarized. Description of how to make light unpolarized by the multi-order λ/4 wavelength plate 121a will be made later. Since it is possible to divide an intensity of light equally all the time by the optical-path splitter 120, it is possible to achieve an image of a brightness which is independent of polarization.

By generating a phase difference of even higher order and making the multi-order λ/4 wavelength plate a super multi-order λ/4 wavelength plate, it is possible to achieve a depolarization effect. A polarized wave for which an intensity of an extraordinary light ray (S-polarized light) and an intensity of an ordinary light ray (P-polarized light) vary at a high frequency in accordance with the wavelength can be deemed as equivalent to unpolarized in a visible range (400 nm to 700 nm).

In a zero-order wavelength plate described in conventional technology or a multi-order wavelength plate of several wavelengths, a split intensity of light transmitted and a split intensity of light reflected in the optical-path splitter vary largely according to a polarization state and a wavelength of incidence on the optical-path splitter, and it is not possible to achieve images of equal intensity.

Conditional expressions (1) and (2) are conditions for achieving depolarization at the multi-order λ/4 wavelength plate in the visible range. In the present embodiment, a wavelength plate which is a multi-order λ/4 wavelength plate which generates a phase difference of 10 to 18 wavelengths for example, and a birefringent material having a birefringence in an appropriate range is used for the multi-order λ/4 wavelength plate. Accordingly, it is possible to achieve a favorable depolarization effect.

When values fall below lower limit values of conditional expressions (1) and (2), the depolarization effect becomes inadequate, and brightness of images split by the optical-path splitter vary according to an observation wavelength and the polarization state, and therefore it is not preferable.

When upper limit values of conditional expressions (1) and (2) are exceeded, the λ/4 wavelength plate is excessively thick, and a front-end portion of endoscope becomes large in size. Furthermore, the birefringence being excessively high, a focusing position of the ordinary light and a focusing position of the extraordinary light are shifted largely, thereby leading to degradation of a quality of combined image.

Moreover, according a preferable aspect of the present embodiment, it is desirable that the λ/4 wavelength plate 121a is adhered to an isotropic plate material 121g (refer to FIG. 4) such as an optical glass.

When the birefringence Δn of the birefringent material used for the λ/4 wavelength plate 121a is in a range of 0.9 to 0.23, an embodiment of a comparatively thin thickness exists. For example, in a case of preparing a multi-order λ/4 wavelength plate of 10 wavelengths by using LiNbO$_3$ (lithium niobate), a thickness thereof becomes approximately 62 μm.

Moreover, the λ/4 wavelength plate 121a may be disposed on an image-side surface of an aperture stop S.

For instance, in a case of preparing a multi-order λ/4 wavelength plate of the same 10 wavelengths by using YVO$_4$ (yttrium orthovanadate), a thickness thereof becomes approximately 24 μm, and necessitates careful handling in order to prevent damage.

Thus, the λ/4 wavelength plate as a single plate being weak in mechanical strength, it is desirable to maintain the strength by bringing in optical contact with or by adhering to an isotropic plate material such as a normal optical glass having no birefringence.

Figure 4:
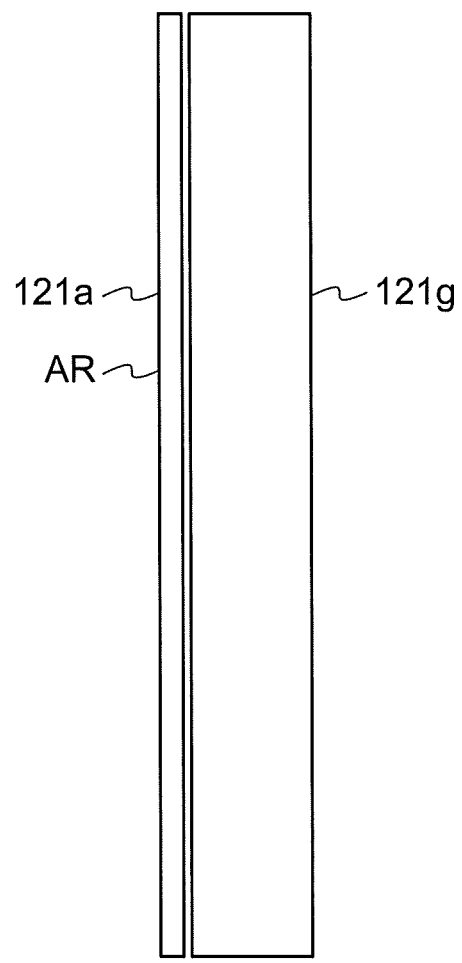
FIG. 4 is a cross-sectional block (arrangement) diagram of the multi-order $\lambda/4$ wavelength plate.

Moreover, according to a preferable aspect of the present embodiment, it is desirable that an anti-reflection coating AR is applied to a surface of the λ/4 wavelength plate 121a (refer to FIG. 4).

The birefringent material in the present embodiment has a comparatively high refractive index of 2 or more than 2, and problems such as a loss of brightness, a ghost, and a flare due to reflection at the surface are susceptible to occur. Therefore, it is desirable to apply the anti-reflecting coating to the surface of the birefringent material. Moreover, in a case of adhering to the isotropic material (the glass plate 121g) as mentioned above, the refractive index of an adhesive being 1.5 in general, an anti-reflection coating on an adhesive surface is also effective.

Moreover, according to a preferable aspect of the present embodiment, it is desirable that the birefringent material of the λ/4 wavelength plate 121a is one of LiNbO$_3$ (lithium niobate), YVO$_4$ (yttrium orthovanadate), calcite, and α-BBO (α-barium borate).

By using crystalline materials having a high birefringence as described above, it is possible to achieve an effective depolarization effect.

Figure 2:
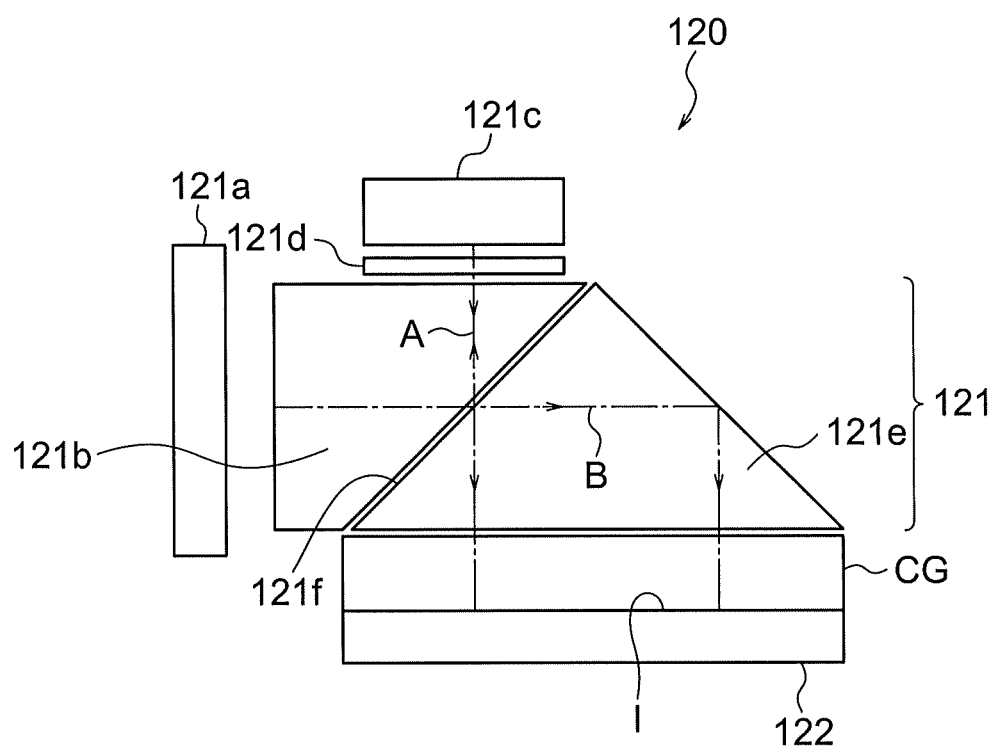
FIG. 2 is a schematic block diagram of a multi-order $\lambda/4$ wavelength plate, the optical-path splitter, and the image sensor in the endoscope (the image pickup apparatus) according to the embodiment.

FIG. 2 is a diagram showing a schematic arrangement of the λ/4 wavelength plate, the optical-path splitter 120, and the image sensor 122.

Light emerged from the objective optical system OBL is incident on the optical-path splitter 120 via the λ/4 wavelength plate 121a. The λ/4 wavelength plate 121a, as it will be described by using FIG. 5, has a function of depolarizing polarized light with a simple arrangement.

The optical-path splitter 120 includes a polarization beam splitter 121 which splits an object image into two optical images having a different focus and the image sensor 122 which acquires two images by picking up the two optical images.

The polarization beam splitter 121, as shown in FIG. 2, includes an object-side prism 121b, an image-side prism 121e, a mirror 121c, and a λ/4 plate 121d. Both the object-side prism 121b and the image-side prism 121e have a beam splitting surface which is inclined at 45 degrees with respect to an optical axis AX.

A polarization splitting film 121f is formed on the beam splitting surface of the object-side prism 121b. Moreover, the object-side prism 121b and the image-side prism 121e form the polarization beam splitter by bringing in contact the beam splitting surfaces thereof via the polarization splitting film 121f.

Moreover, the mirror 121c is provided near an edge surface of the object-side prism 121b via the λ/4 plate 121d. The image sensor 122 is attached to an edge surface of the image-side prism 121e via a cover glass CG. Here, I is an image forming surface (image pickup surface).

An object image from the objective optical system OBL is split into an S-polarized light component (reflected light) and a P-polarized light component (transmitted light) by the polarization splitting film 121f provided to the beam splitting surface of the object-side prism 121b, and is split into two optical images which are an optical image on a reflected-light side and an optical image on a transmitted-light side.

The optical image of the S-polarized light component is reflected at the polarization splitting film 121f toward a side facing the image sensor 122 and follows an optical path A, and upon being transmitted through the λ/4 plate 121d, is reflected at the mirror 121c and is returned toward the image sensor 122. An angle of polarization of the optical image returned is turned by 90°, by being transmitted again through the λ/4 plate 121d, and upon being transmitted through the polarization splitting film 121f is formed as an image on the image sensor 122.

The optical image of the P-polarized light component is transmitted through the polarization splitting film 121f and follows an optical path B, and upon being reflected by a mirror surface provided to an opposite side of the beam splitting surface of the image-side prism 121e which returns perpendicularly toward the image sensor 122, is formed as an image on the image sensor 122. At this time, an optical path in prism glass is set such that a predetermined optical path difference of about tens of μm occurs between the optical path A and the optical path B, and the two optical images with different focus are formed as an image on a light-receiving surface of the image sensor 122.

In other words, the object-side prism 121b and the image-side prism 121e are disposed such that an optical-path length of the reflected-light side becomes shorter (smaller) than an optical-path length (path length in glass) on the transmitted-light side reaching the image sensor 122 in the object-side prism 121b such that the object image can be split into two optical images with different focusing positions.

Figure 3:
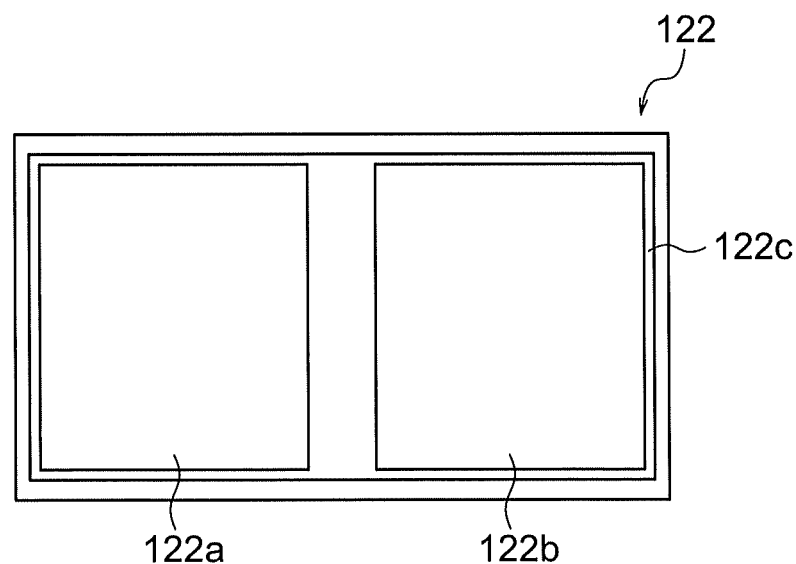
FIG. 3 is a schematic block diagram of the image sensor in the endoscope (the image pickup apparatus) according to the embodiment.

FIG. 3 is a schematic structural diagram of the image sensor 122. The image sensor 122, as shown in FIG. 3, is provided with two light-receiving areas (effective pixel areas) 122a and 122b in an overall pixel area of the image sensor 122 for picking up an image by receiving separately each of the two optical images with different focusing positions.

FIG. 4 shows a cross-sectional view of an arrangement of the λ/4 wavelength plate 121a. The multi-order λ/4 wavelength plate 121a according to an example is in close contact with an isotropic material such as the normal optical glass 121g having no birefringence by optical contact or adhering. Accordingly, a mechanical strength is achieved. An example shown in FIG. 4 is an arrangement example of a multi-order λ/4 wavelength plate of 10 wavelengths having a total thickness of 0.3 mm.

Moreover, the anti-reflection coating AR is applied to an object-side surface of the multi-order λ/4 wavelength plate 121a. Accordingly, it is possible to reduce problems such as the loss of brightness, the ghost, and the flare due to reflection at the surface.

Figure 5A:
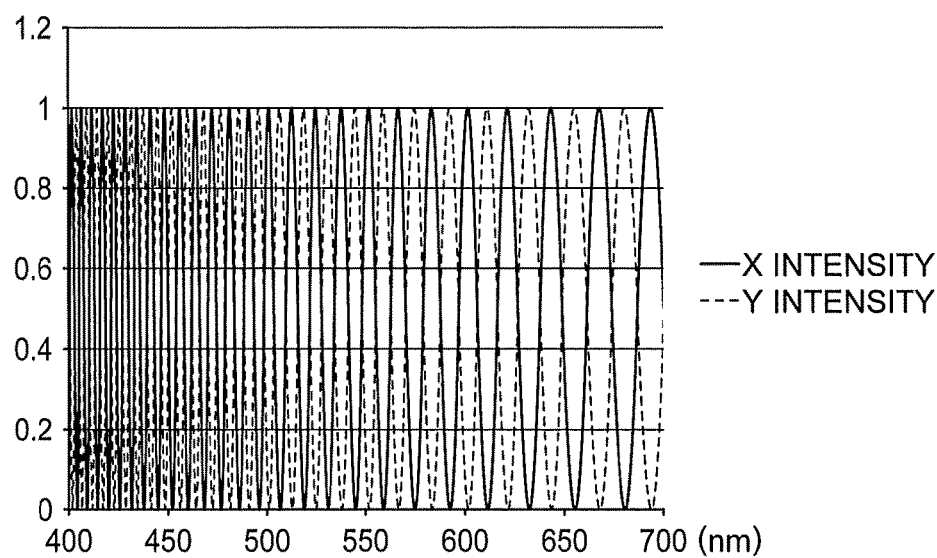
FIG. 5A shows optical characteristics of a multi-order $\lambda/4$ wavelength plate of 28 wavelengths.
Figure 5B:
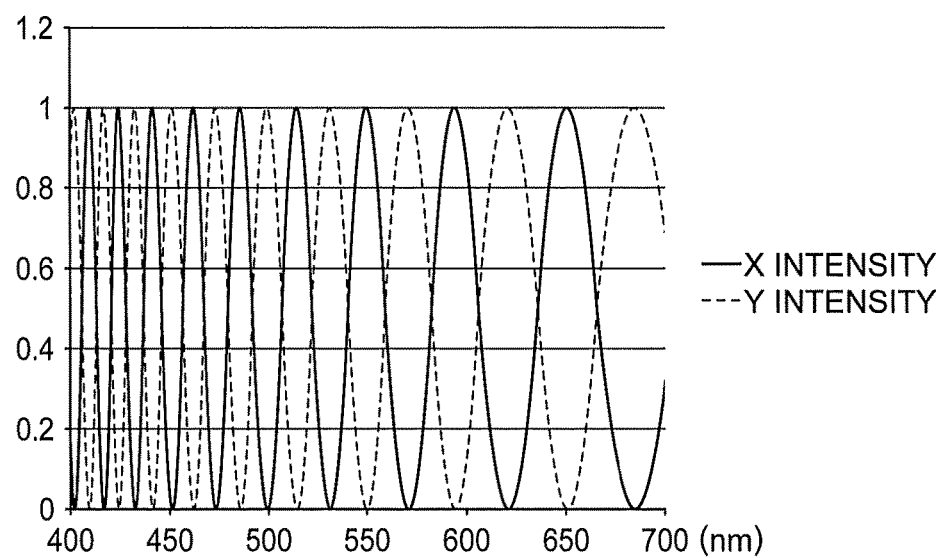
FIG. 5B shows optical characteristics of a multi-order $\lambda/4$ wavelength plate of 10 wavelengths.
Figure 5C:
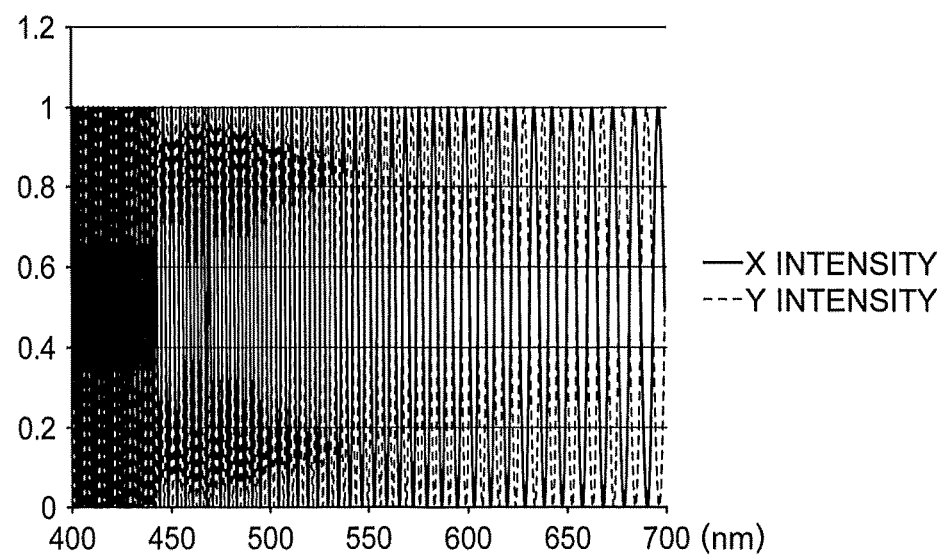
FIG. 5C shows optical characteristics of a multi-order $\lambda/4$ wavelength plate of 85 wavelengths.

Next, FIG. 5A, FIG. 5B, and FIG. 5C show optical characteristics of the multi-order λ/4 wavelength plate 121a in the endoscope. Solid lines (intensity X) and dashed lines (intensity Y) indicate orthogonal polarized light components respectively. A horizontal axis indicates a wavelength (nm) and a vertical axis indicate an intensity of each of the P-polarized light (intensity X for example) and the S-polarized light (intensity Y for example) after being transmitted through the multi-order λ/4 wavelength plate 121a. The multi-order λ/4 wavelength plate 121a having a high birefringence is disposed between the polarization light beam splitter 121 and the objective optical system OBL of the endoscope, and used as a depolarization plate. Since the polarized wave varies at an extremely high frequency according to the wavelength, the multi-order λ/4 wavelength plate 121a can be deemed as equivalent to an unpolarized in the visible range (400 nm to 700 nm).

In a multi-order λ/4 wavelength plate of zero order or of several wavelengths, although it is possible to convert a linearly polarized light of a specific wavelength to a circularly polarized light, since dependence on wavelength and dependence on polarization being high, it is not possible to maintain a splitting strength in the polarization beam splitter constant all the time, and it is not possible to achieve an image with uniform intensity. By making the arrangement shown in the present example, an adequate depolarization effect is achieved, and it is not necessary to use a depolarization plate having a complex arrangement. Consequently, an action effect that it is possible to realize small-sizing of a front-end portion of the endoscope system is shown.

Example A, FIG. 5A

Figure 6:
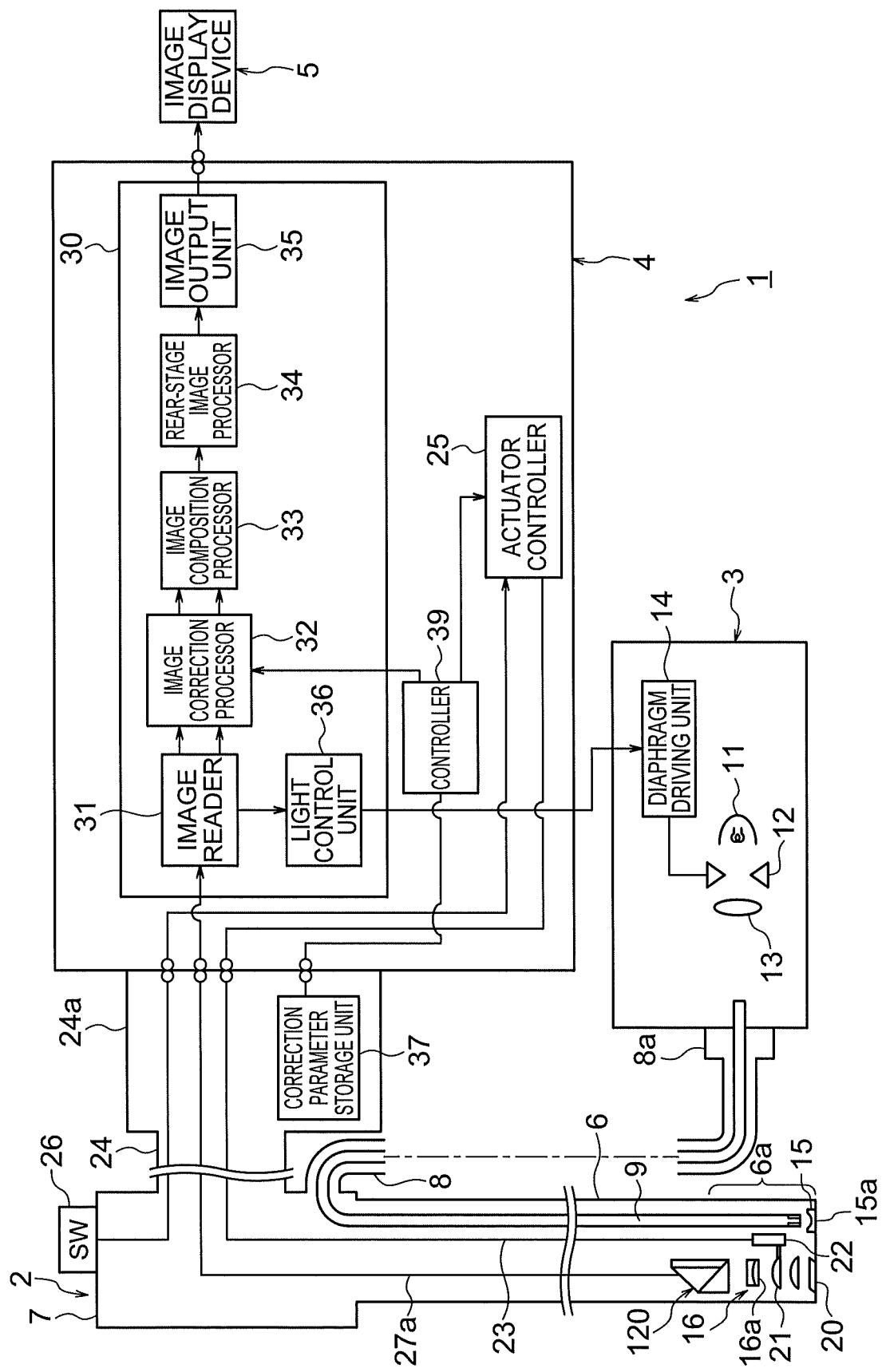
FIG. 6 is a functional block diagram showing an arrangement of an endoscope system according to an embodiment.

An example of
LiNbO$_3$ single plate, d=0.17 mm
λ/4 wavelength plate that generated a phase difference of 27 wavelengths Example B, FIG. 5B An example of
LiNbO$_3$+glass, d=0.06 (LN)+0.24 (S-BSL7, Manufactured by Ohara Corporation) mm
λ/4 wavelength plate that generated a phase difference of 10 wavelengths Example C, FIG. 5C An example of
YVO$_4$+glass, d=0.2 (Y)+0.2 (S-BSL7, manufactured by Ohara Corporation)
λ/4 wavelength plate that generated a phase difference of 85 wavelengths As illustrated in FIG. 6, an endoscope system 1 according to the present embodiment includes an endoscope 2 inserted into a subject, a light source 3 configured to supply illumination light to the endoscope 2, a processor 4, and an image display device 5.

The processor 4 has a function of performing image processing, but also has other functions. The processor 4 includes an actuator controller 25, an image processor 30, and a controller 39. The image display device 5 displays an image signal generated with the processor 4 as an endoscope image.

The endoscope 2 includes an elongated insertion unit 6 to be inserted into the subject, and an operating unit 7 provided at the rear end of the insertion unit 6. A light guide cable 8 extends outward from the operating unit 7. One end of the light guide cable 8 is detachably connected with the light source 3 through a connection unit 8a. The light guide cable 8 includes a light guide 9 therein. Part of the light guide 9 is disposed inside the insertion unit 6.

The light source 3 includes therein a lamp 11, such as a xenon lamp, as the light source. The light source is not limited to the lamp 11, such as a xenon lamp, but a light emitting diode (abbreviated to "LED") may be used. The transmitted light quantity of the illumination light generated with the lamp 11, for example, white light, is regulated with a diaphragm 12. Thereafter, the illumination light is condensed with a condenser lens 13, and made incident on an incident end surface of the light guide 9. It is possible to change the aperture of the diaphragm 12 with a diaphragm driving unit 14.

The light guide 9 transmits the illumination light generated by the light source 3 to a distal end portion 6a of the insertion unit 6. The transmitted illumination light is emitted from the distal end surface of the light guide 9. An illumination lens 15 is disposed in the distal end portion 6a while facing the distal end surface. The illumination lens 15 emits the illumination light from an illumination window 15a. In this manner, the observation target region inside the subject is illuminated.

An observation window 20 is provided adjacent to the illumination window 15a in the distal end portion 6a. Light from the observation target region passes through the observation window 20, and is made incident on the inside of the distal end portion 6a. The objective optical system is disposed behind the observation window 20. The objective optical system is formed of a lens group 16 and an optical path splitter 120.

The lens group 16 includes a lens 16a and a lens 21. The lens 21 is movable along the optical axis. In this manner, focusing is performed. An actuator 22 is disposed to move the lens 21.

One image sensor 122 (not illustrated) is disposed on the optical path splitter 120. Two optical images are simultaneously formed on the light-receiving surface of the image sensor 122. The two optical images are imaged with the image sensor 122.

The operating unit 7 is connected with the processor 4 through a cable 24. A signal connector 24a is provided in a portion connected with the processor 4. Transmission of various types of information is performed between the endoscope 2 and the processor 4 through the cable 24. The signal connector 24a includes a correction parameter storage unit 37.

The correction parameter storage unit 37 stores therein correction parameters (or information of correction parameters) used for correction of the image. The correction parameters are different between individual endoscopes. It is assumed that an endoscope having unique endoscope identification information is connected with the processor 4. In this case, on the basis of the endoscope identification information, correction parameters peculiar to the connected endoscope are read from the correction parameter storage unit 37. Image correction is performed in an image correction processor 32 on the basis of the read correction parameters. Presence/absence of correction is determined by the controller 39.

Control of the actuator 22 is performed by the actuator controller 25. For this reason, the actuator 22 and the actuator controller 25 are connected through a signal line 23. Moreover, the image sensor is connected with the image processor 30 through a signal line 27a. The signal from the image sensor is input to the image processor 30. Information of a switch 26 provided in the operating unit 7 is also transmitted to the processor 4 through a signal line.

When the optical path length in the first optical path B is slightly different from the optical path length in the second optical path A, two optical images in focus are formed in front of and behind the image pickup surface. The shift quantities of the optical images from the image pickup surface are slight. For this reason, two optical images in focus only in a part of the region are formed on the image pickup surface.

The two optical images are imaged with the image sensor 122. An image signal acquired by imaging is input to the image processor 30 through the signal line 27a. The image processor 30 includes an image reader 31, the image correction processor 32, an image composition processor 33, a rear-stage image processor 34, an image output unit 35, and a light control unit 36.

In the image reader 31, image signals of a plurality of images are read from the input image signal. Herein, both the number of optical images and the number of images are two.

In the optical system forming two optical images, a geometrical difference may occur. Examples of the geometrical difference include a relative shift (difference) of the two optical images, such as a shift (difference) in magnification, a shift (difference) in position, and a shift (difference) in rotational direction. It is difficult to completely remove these differences in manufacturing of the objective optical system or the like. However, when the shift quantities of them increase, for example, a composite image looks double. For this reason, it is preferable to correct the geometrical difference described above in the image correction processor 32.

The image correction processor 32 performs image correction on the two read images. The image correction processor 32 performs, for example, processing to make at least one difference among a relative difference in magnification, a difference in position, and a difference in rotation agree between the two images.

In addition, the image correction processor 32 performs tone correction. For this reason, the image correction processor 32 includes atone correction unit (not illustrated). In tone correction, the tone correction unit performs processing to make relative luminance and saturation of the two images substantially agree in at least one desired specific wavelength band. The tone correction may be performed by the image correction processor 32, without providing the tone correction unit.

The image correction processor 32 changes the luminance in one of the two images to substantially agree with the luminance in the other image. Moreover, the image correction processor 32 changes the saturation in one of the images to substantially agree with the saturation in the other image.

As described above, in a method of acquiring an image with a large depth of field, only in-focus regions are extracted from a plurality of images, and composition of the extracted regions is performed. In the endoscope according to the present embodiment, it is possible to reduce a difference in brightness and/or a difference in tone in a plurality of images. Accordingly, it is possible to reduce unevenness in brightness and/or a difference in tone in the composite image.

Moreover, in a method for improving the color reproducibility of the image, image composition using two images is performed. When a difference in brightness and a difference in tone occurs in two optical images, a difference in brightness and a difference in tone occurs also in two images acquired by imaging. In the endoscope according to the present embodiment, it is possible to reduce a difference in brightness and a difference in tone, even when a difference in brightness and a difference in tone occurs in a plurality of images. Accordingly, it is possible to further improve color reproducibility of the composite image.

In the image composition processor 33, first, contrast is compared using two images. This comparison is performed on each of the spatially equal pixel regions in the two images. Thereafter, the pixel region with the relatively high contrast is selected. Thereafter, one image is generated using the selected pixel region. As just described, one composite image is generated from two images. When a difference in contrast between two images is small, it suffices to generate a composite image after performing composite image processing to provide each of the images with a predetermined weight and add the weight to the images.

The rear-stage image processor 34 performs image processing, such as edge enhancement and gamma correction, on the composite image. The image output unit 35 outputs the image-processed image to the image display device 5.

In the light control unit 36, a light control signal to control brightness of light to the standard brightness is generated from the image read with the image reader 31. The light control signal is output to the diaphragm driving unit 14 of the light source 3. The diaphragm driving unit 14 regulates the opening quantity of the diaphragm 12 so as to maintain the standard brightness in accordance with the light control signal.

Next, in the present embodiment, a flow in a case of combining two optical images will be described below according to a flowchart in FIG. 7.

An image related to the far-point image and an image related to the near-point image with a different focus are acquired in the image sensor 122. At step S101, the two images which are the near-point image and the far-point image, are subjected to correction processing. In other words, according to correction parameters that have been set in advance, correction of two images is carried out such that the relative position, the relative angle, and the relative magnification of each optical image of the two images becomes substantially same. This correction processing is carried out in the image correction processor 32. Images after correction are output to the image composition processor 33. The brightness and color of the two images may be corrected according to the requirement.

At step S102, the image composition processor 33 synthesizes the two images subjected to the correction processing. In other words, for the pixel area corresponding to each of the far-point image and the near-point image, a contrast value is calculated, and the contrast values are compared.

At step S103, a judgment of whether or not there is a difference in the contrast values that have been compared is made. In a case in which there is a difference in the contrast, the process advances to step S105. At step S105, the image combining is carried out. In a case in which there is a difference in the contrast, an area with a high contrast value is selected, and the images are combined.

In a case in which there is no difference in the contrast or in a case in which the difference in the contrast is small, the process advances to step S104.

In a case in which the difference in the contrast values is small or in a case in which the contrast values are almost same, it is necessary to make a judgment which to select between the two images which are the far-point image and the near-point image. Wrong choice of the selection becomes a cause of unstable processing. For instance, in a case in which a selected image includes a fluctuation in a signal such as noise, a discontinuous area occurs in the combined image or a problem such that an object image which is resolved originally becomes blurred occurs.

Therefore, the process advances to step S104 and the weighting is carried out. At step S104, in the pixel area in which the contrast is compared, in a case in which the contrast values for the two images which are the far-point image and the near-point image almost same, the weighting is carried out. Moreover, the instability of the image selection is eliminated by carrying out an addition processing of images subjected to weighting at the subsequent step S105.

In such manner, according to the present embodiment, in both the close observation and the distant observation, it is possible to acquire an image in which the depth of field has been widened, while preventing the blurring of the optical image and the occurrence of the discontinuous area in the combined image due to noise.

FIG. 8 is a diagram showing an image-formation state in a case in which an image is formed on an image sensor after reflection for odd number of times by the polarization beam splitter 121. In a case of the abovementioned polarization beam splitter 121 in FIG. 8, an optical image is formed on the image sensor 122 after one reflection or in other words after reflection for the odd number of times. Consequently, one of the two images assume an image-formation state (mirror image) as shown in FIG. 8, and an image processing in which an image direction is made to coincide by inverting the mirror image in the image processor 30, is carried out.

Since correction of the mirror image by an optical reflection for the even number of times may lead to making the objective optical system large-size and the cost of the prism high, it is preferable to carryout the correction of the mirror image by reflection for the odd number of times by inverting the mirror image in the image correction processing section 32.

In a case in which the image sensor 122 has a shape which is long in a longitudinal direction of the endoscope, it is preferable to rotate the combined image appropriately up on taking into consideration an aspect ratio of the image display device 5.

An objective optical system in an endoscope (image pickup apparatus) according to an example of the present invention will be described below.

Figure 9A:
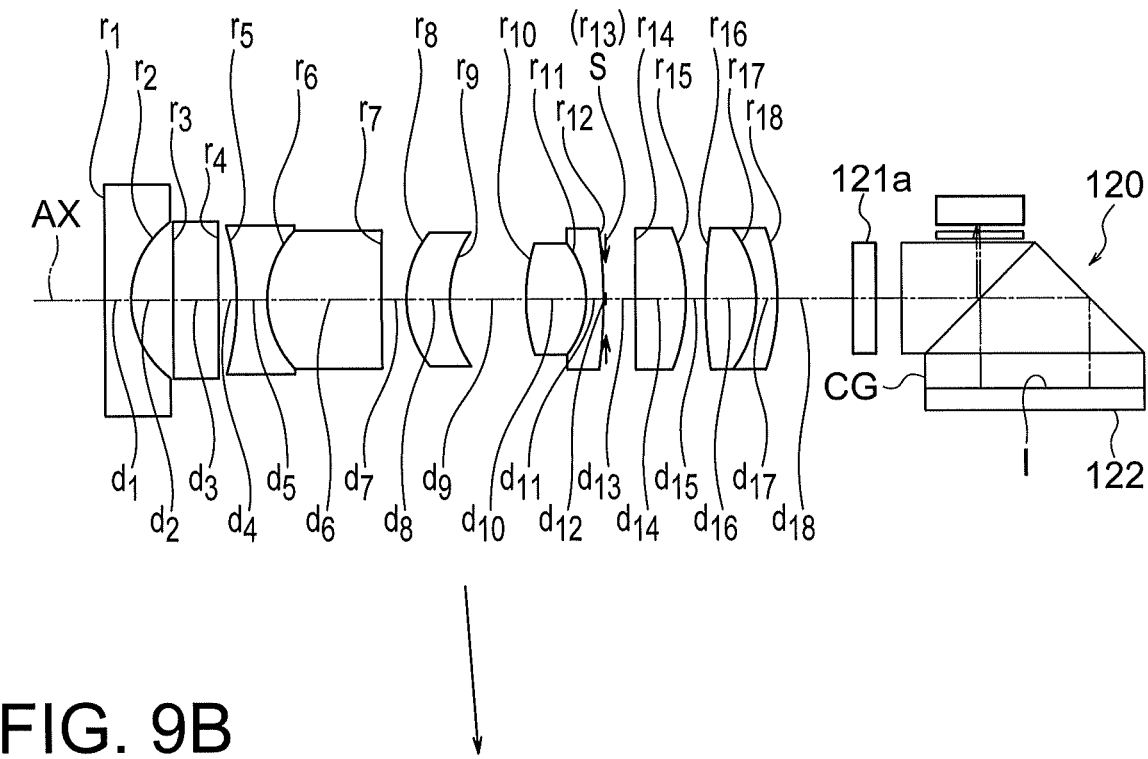
FIG. 9A and FIG. 9B are cross-sectional views of an arrangement of an objective optical system, an optical-path splitter, and an image sensor in an endoscope according to an example 1, where.
Figure 9B:
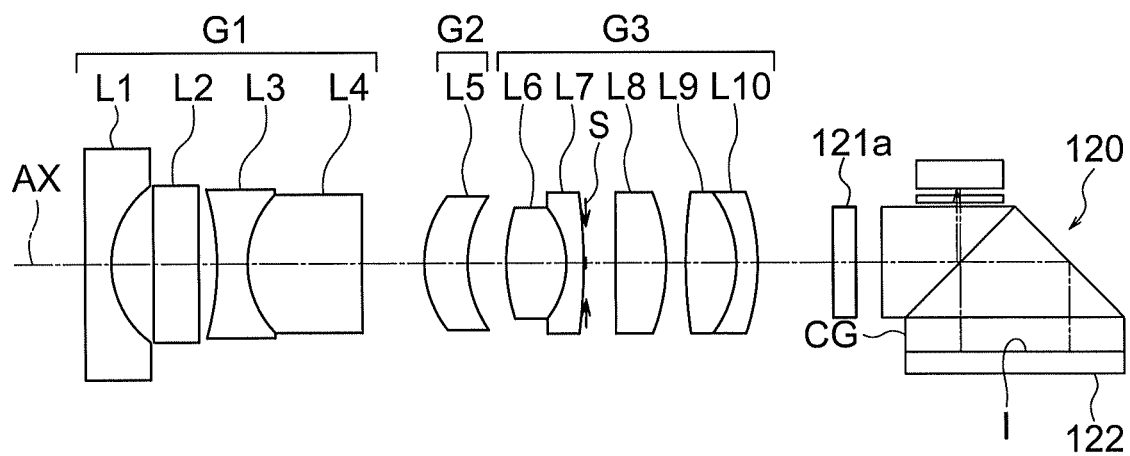

FIG. 9A and FIG. 9B are diagrams showing cross-sectional views of an arrangement of the objective optical system, a λ/4 wavelength plate, an optical-path splitter, and an image sensor. Here, FIG. 9A is a diagram showing a cross-sectional view of the objective optical system in a normal observation state (an object point at a far distance). FIG. 9B is a diagram showing a cross-sectional view of the objective optical system in a close observation state (an object point at a near distance).

The objective optical system of the present example includes in order from an object side to an image side, a first lens group G1 having a negative refractive power, a second lens group G2 having a positive refractive power, and a third lens group G3 having a positive refractive power. Moreover, an aperture stop S is disposed in the third lens group G3. The second lens group G2 moves toward an image side on an optical axis AX, and corrects a variation in a focal position due to a change from the normal observation state to the close observation state.

The first lens group G1 includes in order from the object side to the image side, a planoconcave negative lens L1 having a flat surface directed toward the object side, a plan parallel plate L2, a biconcave negative lens L3, and a positive meniscus lens L4 having a convex surface directed toward an image side. Here, the biconcave negative lens L3 and the positive meniscus lens L4 are cemented. The second lens group G2 includes a positive meniscus lens L5 having a convex surface directed toward the object side. The third lens group G3 includes in order from the object side to the image side, a biconvex positive lens L6, a negative meniscus lens L7 having a convex surface directed toward the image side, an aperture stop S, a biconvex positive lens L8, a biconvex positive lens L9, and a negative meniscus lens L10 having a convex surface directed toward the image side. Here, the biconvex positive lens L6 and the negative meniscus lens L7 are cemented. The biconvex positive lens L9 and the negative meniscus lens L10 are cemented.

The abovementioned λ/4 wavelength plate 121a and the optical-path splitter 120 are disposed on the image side of the third lens group G3. An optical path is bent at a prism in the optical system. The plane parallel plate is a filter having applied thereto a coating for cutting off light of specific wavelengths such as 1060 nm of YAG (yttrium aluminum garnet) laser, 810 nm of semiconductor laser, or light of infrared region. Here, I is an image forming surface (image pickup surface).

The λ/4 wavelength plate 121a is disposed in an optical path up to the optical-path splitter 120 on the object side of the third lens group G3.

Numerical data of each example is shown below. Regarding symbols, r denotes a radius of curvature of each lens surface, d denotes a distance between lens surfaces, ne denotes a refractive index for an e-line of each lens, ve denotes Abbe's number for each lens, FNO denotes an F-number, and ω denotes a half angle of view. Moreover, a back focus fb is a distance from an optical surface nearest to image up to a paraxial image plane expressed upon being subjected to air conversion. A total length is a length obtained upon adding the back focus to a distance (not subjected to air conversion) from a lens surface nearest to object up to an optical surface nearest to image. A stop is an aperture stop.

Example 1

| Unit mm | | | | |
|---|---|---|---|---|
| Surface data | | | | |
| Surface no. | r | d | ne | ve |
| 1 | ∞ | 0.49 | 1.88815 | 40.52 |
| 2 | 1.812 | 0.79 | | |
| 3 | ∞ | 0.84 | 1.52300 | 66.3 |
| 4 | ∞ | 0.34 | | |
| 5 | −4.881 | 0.56 | 1.88815 | 40.52 |
| 6 | 1.866 | 2.13 | 1.85504 | 23.59 |
| 7 | 77.332 | Variable | | |
| 8 | 2.010 | 0.81 | 1.48915 | 70.04 |
| 9 | 2.149 | Variable | | |
| 10 | 3.354 | 1.13 | 1.65222 | 33.53 |
| 11 | −1.665 | 0.32 | 2.01169 | 28.07 |
| 12 | −9.987 | 0.04 | | |
| 13(Stop) | ∞ | 0.56 | | |
| 14 | 512.363 | 0.95 | 1.70442 | 29.89 |
| 15 | −3.552 | 0.36 | | |
| 16 | 9.128 | 0.94 | 1.48915 | 70.04 |
| 17 | −2.180 | 0.39 | 1.93429 | 18.74 |
| 18 | −4.093 | 4.59 | | |
| 19(Image pickup surface) | ∞ | | | |

| Various data | | |
|---|---|---|
| | Normal observation state | Close observation state |
| Focal length | 1.00 | 1.01 |
| FNO. | 3.58 | 3.53 |
| 2ω | 144.9 | 139.4 |
| fb (in air) | 4.59 | 4.59 |
| Total length(in air) | 17.15 | 17.05 |
| d7 | 0.47 | 1.20 |
| d9 | 1.43 | 0.70 |

Unit focal length
First unit f1 = −1.12
Second unit f2 = 21.78
Third unit f3 = 3.51
Conditional Expression
(1) (d/d0) × 0.25
(2) |Δn|

| | Example1 | Example2 | Example3 |
|---|---|---|---|
| (1) | 27.4 | 10.0 | 84.7 |
| (2) | 0.08798 | 0.08798 | 0.23122 |
| Crystal material | LiNbO$_3$ | LiNbO$_3$ | YVO$_4$ |
| d (mm) | 0.1700 | 0.0620 | 0.2 |
| d0 | 0.0016 | 0.0016 | 0.0006 |
| Δn | −0.087980025 | −0.087980025 | 0.231221658 |

| | Example4 | Example5 | Example6 |
|---|---|---|---|
| (1) | 42.3 | 83.9 | 10.0 |
| (2) | 0.23122 | 0.08798 | 0.23122 |

-continued

| Unit mm | | | |
|---|---|---|---|
| Crystal material | YVO$_4$ | LiNbO$_3$ | YVO$_4$ |
| d (mm) | 0.1000 | 0.5210 | 0.0235 |
| d0 | 0.0006 | 0.0016 | 0.0006 |
| Δn | 0.231221658 | −0.087980025 | 0.231221658 |

| | Example7 | Example8 |
|---|---|---|
| (1)' | 16.1 | 48.3 |
| (2) | 0.08798 | 0.08798 |
| Crystal material | LiNbO$_3$ | LiNbO$_3$ |
| d (mm) | 0.1000 | 0.3000 |
| d0 | 0.0016 | 0.0016 |
| Δn | −0.087980 | |

Values corresponding to conditional expressions of the multi-order λ/4 wavelength plate 121a of eight examples 1, 2, 3, 4, 5, 6, 7, and 8 to be used in common in the abovementioned objective optical system are shown below.

$(d/d0) \times 0.25$      Conditional expression (1)

$|\Delta n|$      Conditional expression (2)

$d0 = ((\lambda/10^{-6}) \times 0.25/\Delta n)$ (nm)

Δn=ne−no (difference between a refractive index of an ordinary light ray for the e-line and a refractive index of an extraordinary light ray for the e-line)

Moreover, according to a preferable aspect of the present embodiment, it is desirable to satisfy the following conditional expression (1)' instead of conditional expression (1).

$16 \leq (d/d0) \times 0.25 \leq 48$      (1)'

A lower limit value of conditional expression (1)' is a value in a case in which an ease of thinning processing of the wavelength plate (associated with a cost) has priority (for example, d=0.1 mm).

An upper limit value of conditional expression (1)' is a limit on a mechanical strength at the time of mounting the wavelength plate, and is a value in a case in which an amount of shift in a focusing position of ordinary light and extraordinary light is restricted to smaller amount. By a value falling below the upper limit value of conditional expression (1)', it is possible to achieve a multi-order wavelength plate which is inexpensive and for which a risk of damage is low, and a shift in the focusing position of the ordinary light and the extraordinary light is small, and which enables to achieve an adequate depolarization effect. Conditional expression (2) to be combined with conditional expression (1)' can be used as it is. Conditional expression (1)' is applicable to examples (4), (7), and (8).

Characteristics (a) to (h) of respective examples will be described below.

(a) The example 1 is a typical example of the present embodiment, and is an example in which the wavelength plate is thinned while achieving adequate depolarization effect.

(b) The example 2 is an example in which the wavelength plate is subjected to thinning processing while achieving the minimum depolarization effect, and the mechanical strength is improved by adhering the wavelength plate to a glass.

(c) The example 3 is an example in which the crystalline material of the wavelength plate is changed to YVO$_4$ crystals having a higher birefringence with emphasis on the depolarization effect.

(d) The example 4 is an example in which the thickness of the wavelength plate of the example 3 is changed and a difference in the focusing position for the ordinary light and the focusing position for the extraordinary light due to the birefringence is made small, and is balanced to achieve the adequate depolarization effect.

(e) The example 5 is an example in which the wavelength plate is made thick with an objective of an ease of manual handling, and a cost reduction is facilitated by making the wavelength plate of a single plate.

(d) The example 6 is an example in which the wavelength plate is thinned further while improving the depolarization effect by using YVO$_4$ crystals, and small-sizing of the front-end portion of endoscope is facilitated.

(e) The example 7 is an example in which the degree of difficulty of thinning processing is lowered, and the cost is reduced, and the mechanical strength is improved by adhering to the glass.

(f) The example 8 is an example in which the mechanical strength is favorable and the wavelength plate is made of a single plate.

Various embodiments of the present invention have been described heretofore. However, the present invention is not restricted to the embodiments described heretofore, and embodiments in which the arrangements of the abovementioned embodiments are combined appropriately without departing from the scope of the invention are also within the scope of the present invention.

(Note)

The following arrangement is derived from the examples described above.

(Appended Mode 1)

A multi-order λ/4 wavelength plate made of a birefringent material, wherein the multi-order λ/4 wavelength plate satisfies the following conditional expressions (1) and (2)

$10 \leq (d/d0) \times 0.25 \leq 85$      (1)

$0.09 < |\Delta n| < 0.23$      (2)

where, d denotes a thickness of the multi-order λ/4 wavelength plate, d0 denotes a thickness of the multi-order λ/4 wavelength plate, which becomes zero-order for an e-line, and Δn denotes a birefringence for the e-line of the multi-order λ/4 wavelength plate.

The abovementioned objective optical system may satisfy a plurality of arrangements simultaneously. Making such arrangement is preferable for achieving a favorable endoscope, an image pickup apparatus, and an endoscope system. Moreover, a combination of the preferable arrangements is arbitrary. Furthermore, regarding each conditional expression, an upper limit value or a lower limit value of a numerical range of a further restricted conditional expression may be restricted.

As described heretofore, the present invention is useful for a compact endoscope and an image pickup apparatus which enable to achieve an adequate depolarization effect without a need of using a depolarization plate having a complicated arrangement.

The present invention shows an effect that it is possible to provide a compact endoscope and an image pickup apparatus in which it is possible to achieve an adequate depolarization effect without a need of using a depolarization plate having a complicated arrangement.

What is claimed is:

1. An endoscope comprising, in order from an object side to an image side:
   an objective optical system;
   an optical-path splitter which splits light from the objective optical system into two; and
   an image sensor configured to pick up two split images, wherein:
   a multi-order λ/4 wavelength plate made of a birefringent material is disposed in an optical path between the objective optical system and the optical-path splitter, and
   the multi-order λ/4 wavelength plate satisfies the following conditional expressions (1) and (2)'

$$10 \leq (d/d0) \times 0.25 \leq 85 \quad (1)$$

$$0.08 < |\Delta n| < 0.24 \quad (2)'$$

where,
   d denotes a thickness of the multi-order λ/4 wavelength plate,
   d0 denotes a thickness of the multi-order λ/4 wavelength plate, which is zero-order for an e-line, and
   Δn denotes a birefringence for the e-line of the multi-order λ/4 wavelength plate.

2. The endoscope according to claim 1, wherein the multi-order λ/4 wavelength plate is adhered to an isotropic plate material.

3. The endoscope according to claim 1, wherein an anti-reflection coating is applied to a surface of the multi-order λ/4 wavelength plate.

4. The endoscope according to claim 1, wherein the birefringent material of the multi-order λ/4 wavelength plate is one of $LiNbO_3$, $YVO_4$, calcite, and α-barium borate.

5. The image pickup apparatus according to claim 1, wherein the birefringent material of the multi-order λ/4 wavelength plate is one of $LiNbO_3$, $YVO_4$, calcite, and α-barium borate.

6. An image pickup apparatus comprising, in order from an object side to an image side:
   an objective optical system;
   an optical-path splitter which splits light from the objective optical system into two; and
   an image sensor which picks up two split images, wherein:
   a multi-order λ/4 wavelength plate made of a birefringent material is disposed in an optical path between the objective optical system and the optical-path splitter, and
   the multi-order λ/4 wavelength plate satisfies the following conditional expressions (1) and (2)'

$$10 \leq (d/d0) \times 0.25 \leq 85 \quad (1)$$

$$0.08 < |\Delta n| < 0.24 \quad (2)'$$

where,
   d denotes a thickness of the multi-order λ/4 wavelength plate,
   d0 denotes a thickness of the multi-order λ/4 wavelength plate, which is zero-order for an e-line, and
   Δn denotes a birefringence for the e-line of the multi-order λ/4 wavelength plate.

7. The image pickup apparatus according to claim 6, wherein the multi-order λ/4 wavelength plate is adhered to an isotropic plate material.

8. The image pickup apparatus according to claim 6, wherein an anti-reflection coating is applied to a surface of the multi-order λ/4 wavelength plate.

* * * * *